United States Patent [19]

Varma et al.

[11] Patent Number: 4,711,900

[45] Date of Patent: Dec. 8, 1987

[54] CERTAIN ARYLALKYL OR PYRIDYLALKYL HYDROXAMATES USEFUL FOR TREATING ALLERGIES AND ASTHMA

[75] Inventors: Ravi K. Varma, Belle Mead; Eric M. Gordon, Pennington, both of N.J.

[73] Assignee: E. R. Squibb & Sons, Inc., Princeton, N.J.

[21] Appl. No.: 888,616

[22] Filed: Jul. 23, 1986

[51] Int. Cl.$^4$ .................... C07C 83/10; C07D 213/64; A61K 31/235; A61K 31/44

[52] U.S. Cl. ..................... 514/351; 514/507; 514/575; 260/500.5 H; 260/501.1; 260/501.11; 546/291; 562/452

[58] Field of Search ........................ 546/291; 562/452; 514/351, 346, 563, 575; 260/500.5 H, 501.1, 501.11

[56] References Cited

U.S. PATENT DOCUMENTS 4,242,273 12/1980 Shepherd .......................... 260/453
4,440,940 4/1984 Shepherd ........................... 560/19

OTHER PUBLICATIONS

Corey et al., "Rationally Designed, Potent Competitive Inhibitors of Leukotriene Biosynthesis", J. Am. Chem. Soc., 1984, 106, 1503–1504.

*Primary Examiner*—Alan L. Rotman
*Attorney, Agent, or Firm*—Lawrence S. Levinson; Burton Rodney

[57] ABSTRACT

Arylhydroxamates are provided having the structure

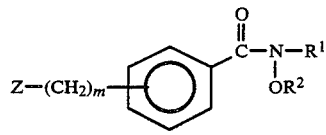

wherein
$R^1$ is hydrogen, lower alkyl, aryl, lower alkenyl, cycloalkyl, or aralkyl;
$R^2$ is hydrogen, lower alkyl, aryl, cycloalkyl, alkanoyl or aroyl;
m is 2 to 8; and Z is 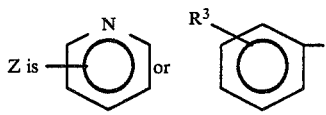

wherein
$R^3$ is OH, COOH

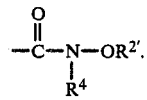

These compounds are useful as inhibitors of $\Delta^5$-lipoxygenase and as such are useful as antiallergy agents.

13 Claims, No Drawings

CERTAIN ARYLALKYL OR PYRIDYLALKYL HYDROXAMATES USEFUL FOR TREATING ALLERGIES AND ASTHMA

DESCRIPTION OF THE INVENTION

The present invention relates to arylhydroxamates which are inhibitors of $\Delta^5$-lipoxygenase and as such are useful, for example, as antiallergy agents and for treating bronchial asthma. These compounds have the structural formula

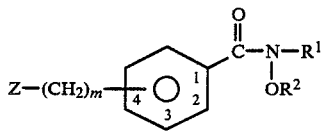

wherein $R^1$ is hydrogen, lower alkyl, aryl, lower alkenyl, cycloalkyl, or aralkyl;

$R^2$ is hydrogen, lower alkyl, cycloalkyl, alkanoyl or aroyl.

m is 2 to 8; and

Z is 2-, 3- or 4-pyridyl or phenyl substituted with OH, COOH or

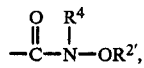

wherein $R^{2'}$ can be any of the radicals set out under the definition of $R^2$, and $R^4$ is H or lower alkyl.

Thus, the compounds of the invention include the following:

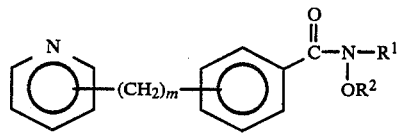

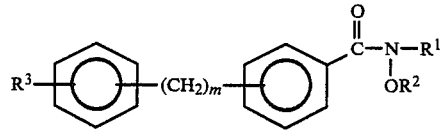

wherein $R^3$ is COOH or

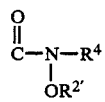

or OH.

The above compounds will form monobasic or dibasic salts. In addition, the compounds of formula I will form salts with dicyclohexylamine as well as with tris(-hydroxymethyl)aminomethane and other amines as set out in U.S. Pat. No. 4,294,759.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as sell as such groups including a halo-substituent, such as F, Br, Cl or I or $CF_3$, an alkoxy substituent, an aryl substituent, an alkyl-aryl substituent, a haloaryl substituent, a cycloalkyl substituent, an alkylcycloalkyl substituent, hydroxy, an alkylamino substitutent, an alkanoylamino substituent, an arylcarbonylamino substituent, a nitro substituent, a cyano substituent, a thiol substituent or an alkylthio substituent.

The term "cycloalkyl" employed herein by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 to 2 halogens, 1 or 2 lower alkyl groups, 1 or 2 lower alkoxy groups, an aryl group, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), 1 or 2 lower alkoxy groups, an aryl group, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" as employed herein by itself or as part of another group includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

The term "alkanoyl" or "aroyl" as used herein by itself or as part of another group refers to a lower alkyl group or an aryl group linked to a carbonyl group.

The term "halogen" or "halo" as used herein refers to chlorine, bromine, fluorine or iodine with chlorine being preferred.

The term "$(CH_2)_m$" includes a straight or branched chain radical having 1 to 7 carbons in the normal chain and may contain one or two lower alkyl and/or one or two halogen substituents. Examples of $(CH_2)_m$ groups include

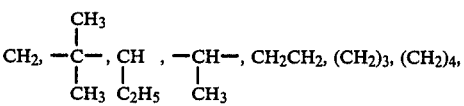

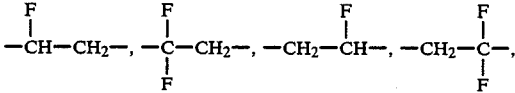

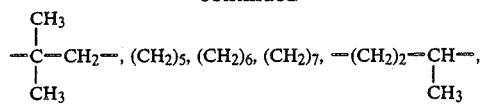
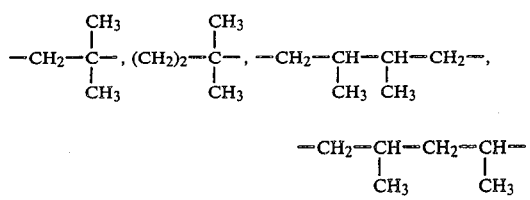
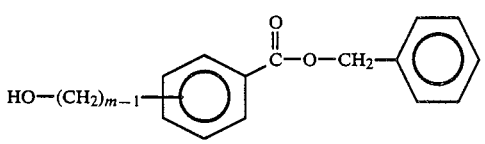

and the like.

Preferred are those compounds of the invention wherein $R^1$ is alkyl, such as methyl, $R^2$ is H, m is 3 to 5; and Z is

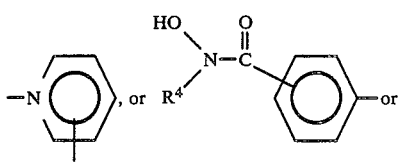

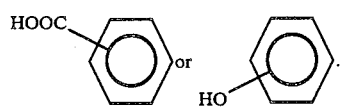

The various compounds of the invention may be prepared as described below.

Compounds of the invention wherein Z is phenyl substituted with an ortho—COOH group, that is

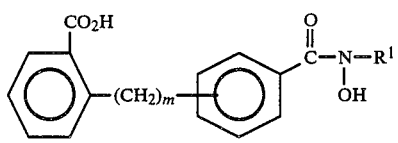    IV may be prepared by esterifying a hydroxyalkyl benzene carboxylic acid of the structure A

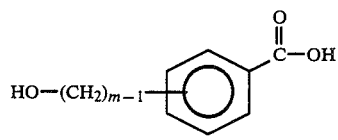    A by reacting A with benzylbromide in the presence of base such as sodium bicarbonate and an inert solvent such as dimethylformamide to form the benzyl ester B

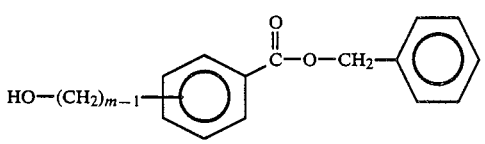    B

Ester B is then oxidized by reacting B with pyridinium chlorochromate in the presence of sodium acetate and methylene chloride to form the aldehyde C

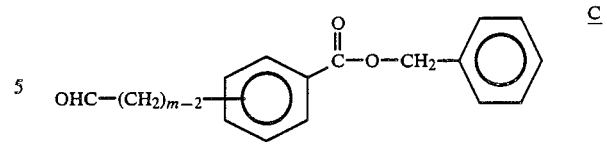    C

Aldehyde C is next reacted with Wittig reagent D

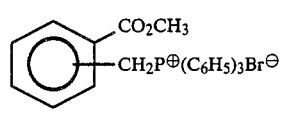    D in the presence of n-butyllithium and an inert solvent such as tetrahydrofuran to form the ester E

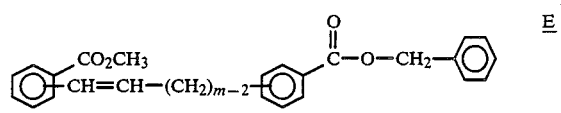    E which is subjected to hydrogenation and hydrogenolysis by treating E with hydrogen in the presence of palladium on carbon or other catalyst to form the acid F

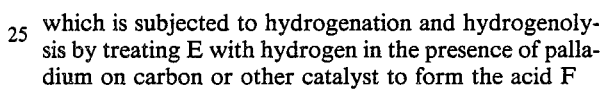    F

Acid F is reacted with oxalyl chloride in the presence of benzene, preferably in the presence of some dimethylformamide, to form acid chloride G

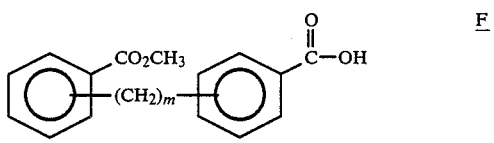    G

Acid chloride G is then converted to the corresponding hydroxamate by treating G with hydroxylamine H

 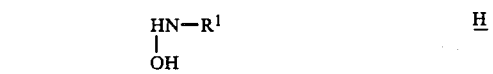    H in the presence of an organic base such as triethylamine and aqueous organic solvent such as tetrahydrofuran or 1,2-dimethoxy ethane to form hydroxamate J

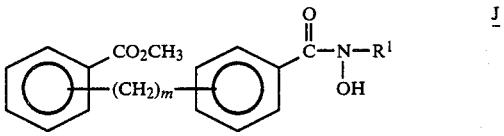    J which is then hydrolyzed by treatment with alkali metal hydroxide such as NaOH or LiOH in the presence of aqueous alcoholic solvent such as methanol or ethanol to form the hydroxamate IV.

The starting Wittig reagent D is prepared by esterifying o-toluic acid by treatment with methyl iodide in the presence of sodium bicarbonate and dimethylformamide to form the corresponding methyl ester which is brominated by treatment with N-bromosuccinimide and azobisisobutyronitrile in benzene to form α-bromo-o-toluic acid methyl ester. The ester is then treated with triphenylphosphine in the presence of acetonitrile or benzene to form D.

Compounds of the invention wherein Z is phenyl substituted with a para—COOH group, that is

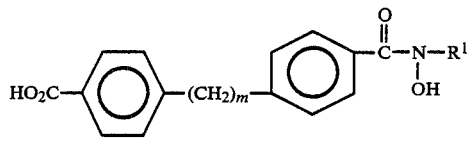

V may be prepared by reacting the phosphorus compound K

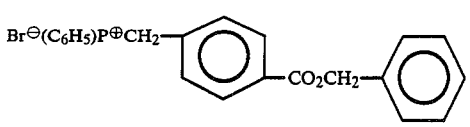

K with aldehyde L

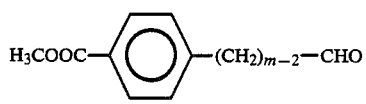

L in a Wittig reaction at reduced temperature in the presence of n-butyllithium and tetrahydrofuran to form the ester M

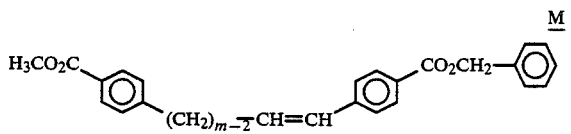

M

Ester M is then converted to the corresponding hydroxamate V employing procedures outlined above in converting ester E to hydroxamate IV.

The starting Wittig reagent K is prepared by esterifying α-bromo-p-toluic acid by treatment with benzyl alcohol, dicyclohexylcarbodiimide and 4-dimethylamino-pyridine in ether and tetrahydrofuran to form the benzyl ester which is then treated with triphenylphosphine in benzene to form K.

The aldehyde L may be prepared by oxidizing the alcohol ester L'

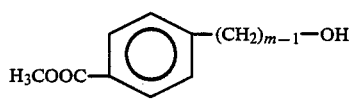

L' by treatment with pyridinium dichlorochromate in the presence of methylene chloride.

Compounds of the invention wherein Z is

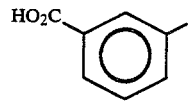

may be prepared by starting from the aldehyde L and α-bromo-m-toluic acid and following the procedure set out above for the preparation of V.

Compounds of the invention wherein Z is

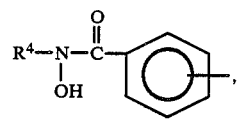

that is

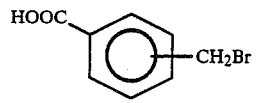

VI may be prepared by reacting acid N

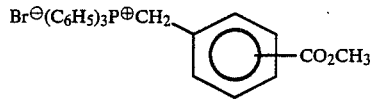

N with diazomethane or ether to form the corresponding ester which is reacted with triphenylphosphine in the presence of benzene to form Wittig reagent O

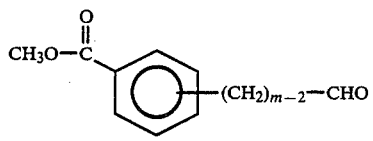

O which is reacted with aldehyde L'

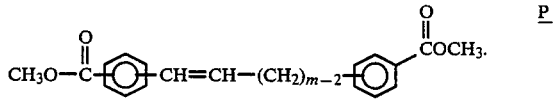

L' in the presence of butyllithium and tetrahydrofuran to form the ester P

P

Ester P is then reduced by treatment with hydrogen in the presence of palladium on carbon and methanol to form the ester O

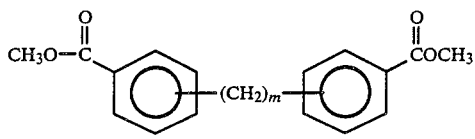

which is hydrolyzed to the corresponding acid R by treatment with alkali metal hydroxide in the presence of methanol to form acid R

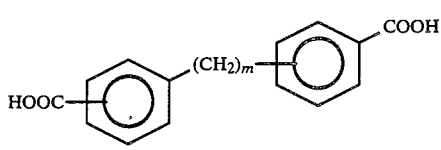

Acid R is converted to the hydroxamate VI

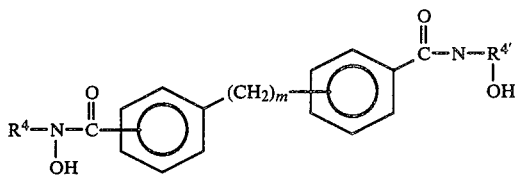

employing procedures similar to that in converting acid F to hydroxamate IV.

Compounds of the invention wherein Z is

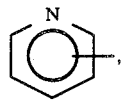

that is compounds of formula II may be prepared by reacting Wittig reagent

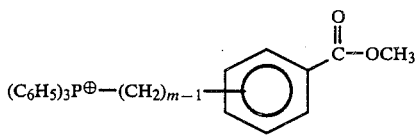

with pyridinecarboxaldehyde S

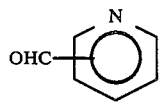

in the presence of potassium t-amylate and tetrahydrofuran or other solvent such as toluene, to form T

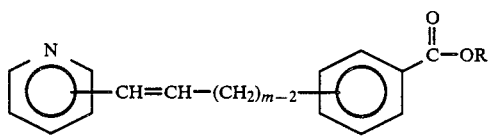

(wherein R is a mixture of

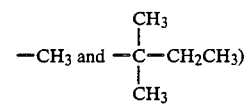

Compound T is then hydrogenated to its reduced form which is hydrolyzed and then converted to the hydroxamate II employing procedures as set out hereinbefore.

Compounds of formula I wherein $R^2$ is alkyl may be prepared from compounds IV, V, VI or VII by treating I with a base such as sodium hydride and an alkyl halide (Hal-Alkyl) in the presence of an inert organic solvent such as tetrahydrofuran and dimethylformamide, to form compounds of the invention VIII

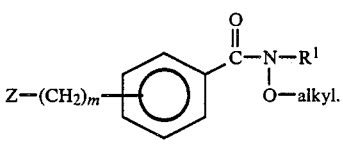

Compounds of formula I wherein $R^2$ is alkanoyl or aroyl may be prepared from compounds IV, V, VI or VII by treating I with an alkanoyl halide, alkanoyl anhydride or aroyl halide in the presence of an organic base such as pyridine to form compounds of the invention IX, where $R^{11}$ is alkyl or aryl

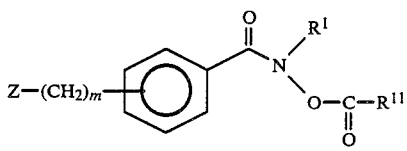

The compounds of the invention are delta-5-lipoxygenase inhibitors and prevent leukotriene $C_4$ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma, bronchial asthma and asthmoid bronchitis.

An effective but essentially non-toxic quantity of the compound is employed in treatment.

The compounds of the invention can be administered orally, parenterally or topically or by aerosol to various mammalian species known to be subject to such maladies, e.g., humans, cattle, horses, cats, dogs, and the like in an effective amount within the dosage range of from about 1 to about 10 mg/kg, preferably from about 1 to about 50 mg/kg and especially about 2 to about 25 mg/kg on a regimen in single or 2 to 4 divided daily doses.

The active substance can be utilized in a composition such as tablet, capsule, solution, cream, lotion, suspension or aerosol containing from about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C. TLC plates were visualized by spraying and heating with 5% phosphomolybdic acid in ethanol. HP-20 refers to a high porous divinylbenzene-polystyrene polymer resin.

EXAMPLE 1

2-[4-[4-[(N-Hydroxy-N-Methylamino)carbonyl]-phenyl]butyl]benzoic acid

A.

(1) o-Toluic acid, methyl ester

A mixture of o-toluic acid (15 g, 0.11 mole), iodomethane (51 g, 0.36 mole) and anhydrous sodium bicarbonate (25.2 g, 0.3 mole) in dry dimethylformamide (60 ml) was stirred at 70° (oil bath temperature) under an atmosphere of nitrogen for 3.5 hours. The resulting mixture was diluted with water (200 ml) and extracted with ethyl ether (3×100 ml). The combined extracts were washed several times with water, dried over anhydrous MgSO$_4$ and evaporated in vacuo to give the title ester compound (15 g, 90.6%) as an oil with a consistent H$^1$-NMR spectrum.

(2) α-Bromo-o-toluic acid, methyl ester

A solution of Parts A(1) acid (15 g, 99.88 mmole), N-bromosuccinimide (18.67 g, 104.87 mmole) and azobisisobutyronitrile (250 mg) in 100 ml of dry benzene was refluxed under an atmosphere of nitrogen for 5 hours and then cooled to room temperature. The precipitated succinimide was removed by filtration. The filtrate was evaporated in vacuo to give title ester compound (20.3 g, 88.7%) as a homogeneous (tlc) oil with a consistent H$^1$-NMR spectrum.

(3) [[2-(Methoxycarbonyl)phenyl]methyl]triphenylphosphonium bromide

A solution of Part A(2) ester compound (11.45 g, 50 mmole) and triphenylphosphine (13.12 g, 50 mmole) in 150 ml of dry acetonitrile was refluxed under an atomsphere of nitrogen for 24 hours. The solvent was evaporated in vacuo. The residue was rinsed with ethyl ether and the ether removed by decantation. The resulting solid was dried over P$_2$O$_5$ in vacuo at 100° overnight to give title compound (20.2 g, 82.2%) with a consistent H$^1$-NMR spectrum.

B.

4-Hydroxypropylbenzoic acid

To a chilled and stirred solution of diisopropylamine (4.63 ml, 33 mmole) in 20 ml of dry tetrahydrofuran at −78° C. (dry ice-acetone bath) under nitrogen was added dropwise 1.7M n-butyllithium in hexane (19.4 ml, 33 mmole). After 20 minutes, a solution of p-toluic acid (2.042 g, 15 mmole) in 20 ml of dry tetrahydrofuran was added dropwise. After strirring at −78° for another 1.5 hours, HMPA (4 ml) was added and then immediately followed by a solution of dry ethylene oxide (2.99 g, 67.9 mmole) in 10 ml of dry tetrahydrofuran. The resulting solution was stirred at −78° for two hours, acidified with 5% hydrochloric acid, warmed up to room temperature and most of the tetrahydrofuran removed in vacuo. The aqueous solution was saturated with sodium chloride and extracted with ethyl ether (3×100 ml). The combined ether extracts were concentrated to 100 ml and extracted with 0.5N sodium hydroxide solution (2×50 ml). This was acidified with 10% hydrochloric acid and extracted with ethyl ether (3×100 ml). The ether extracts were dried over anhydrous MgSO$_4$ and evaporated in vacuo to give a gum. This was chromatographed on a silica gel (120 g, Baker 60–200 mesh) column, eluting successively with dichloromethane-ethyl acetate (9:1 and 1:1), ethyl acetate and dichloromethane-methanol (9:1) to give 750 mg (27.7% solid) of tlc-homogeneous title acid compound with a consistent H$^1$-NMR spectrum.

C.

4-Hydroxypropylbenzoic acid, benzyl ester

A mixture of Part B acid compound (1.35 g, 7.49 mmole), benzyl bromide (1.409 g, 8.24 mmole) and anhydrous sodium bicarbonate (1.57 g, 18.75 mmole) in 15 ml of dry dimethylformamide was stirred at room temperature under an atmosphere of nitrogen overnight. The resulting suspension was diluted with water (50 ml) and extracted with ethyl ether (200 ml). The ether extract was washed several times with water, dried over anhydrous MgSO$_4$ and evaporated in vacuo to give an oil. This was chromatograhed on a silica gel (60 g, Baker 60–200 mesh) column eluting successively with chloroform and chloroform-ethyl acetate (9:1) to give the tlc-homogeneous title ester compound (1.24 g, 61.2%) as an oil with a consistent H$^1$-NMR spectrum.

D.

3-[[4-(Benzyloxycarbonyl)]phenyl]propionaldehyde

To a slurry of HYFLO (3 g, dried in vacuo at 100° overnight), anhydrous sodium acetate (290 mg) of pyridinium chlorochromate (4.68 g) in 25 ml of dry dichloromethane was added dropwise a solution of Part C ester compound (1.24 g, 4.59 mmole) at room temperature under an atmosphere of nitrogen. After stirring for 1.5 hours, the slurry was diluted with ethyl ether (100 ml), filtered through a bed of HYFLO and washed with ethyl ether (50 ml). The filtrate and the washing were combined and washed successively with 0.2M KH$_2$PO$_4$ (25 ml), water (25 ml), 5% CuSO$_4$ (25 ml), water (25 ml), 1.0N KHCO$_3$ (25 ml) and water (25 ml). The organic phase was dried over anhydrous MgSO$_4$ and evaporated in vacuo to give an oil. This was chromatographed on a silica gel (60 g, Baker 60–200 mesh) column eluting successively with ethyl acetate-hexane (5:95, 1:9, and 2:8) to give the tlc-homogeneous title aldehyde compound (855 mg, 69.4%) as an oil with a consistent H$^1$-NMR spectrum.

E.

2-[4-[4-[(Benzyloxy)carbonyl]phenyl]-1-butenyl]benzoic acid, methyl ester

To a chilled and stirred suspension of Part A compound (491.35 mg, 1.0 mmole) in 8 ml of dry tetrahydrofuran (ice bath) was added dropwise n-BuLi (0.5 ml, 0.8 mmole, 1.6M in hexane) under an atmosphere of nitrogen. The suspension became a yellow solution. After stirring in the ice bath for one hour, a solution of Part D compound (134.2 mg, 0.5 mmole) in 2 ml of dry tetrahydrofuran was added dropwise. The solution was then stirred at 0° under an atmosphere of nitrogen for another 4 hours, acidified with 5% hydrochloric acid to pH=2.5, concentrated in vacuo to remove most of the tetrahydrofuran and extracted with ethyl ether (3×30 ml). The combined ether extracts were washed with brine, dried over anhydrous MgSO$_4$ and evaporated in vacuo to give an oil (170 mg). Another run using 720 mg (2.68 mmole) of Part D compound and 2.64 g (5.37 mmole) of Part A compound gave 1.0 g more of an oily product. The oils (1.17 g) were combined and chromatographed on a silica gel (100 g, Baker 60–200 mesh) column eluting with ethyl acetate-hexane (5:95) to give title compound (710 mg, 55.7%) as an oil with a consistent H$^1$-NMR spectrum.

F.

2-[4-[4-(Carboxy)phenyl]butyl]benzoic acid, methyl ester

A solution of Part E compound (710 mg, 1.77 mmole) containing a suspension of palladium on carbon (10%, 200 mg) in 80 ml of methanol was hydrogenated under atmospheric pressure at room temperature for 2 hours and the mixture filtered through a bed of HYFLO to remove the catalyst. The filtrate was evaporated in vacuo to give slightly impure title compound. This was chromatographed on a silica gel (50 g, Baker 60–200 mesh) column eluting successively with chloroform-hexane (9:1) and ethyl acetate-chloroform (5:95) to give the tlc-homogeneous title acid-ester compound (463 mg, 83.6%) as a solid, melting point 120°–122°, with a consistent H$^1$-NMR spectrum.

G.

2-[4-[4-(Chloro)carbonyl]phenyl]butylbenzoic acid, methyl ester

To a chilled (0°, ice bath) and stirred solution to Part F acid compound (460 mg, 1.47 mmole) in a mixture of benzene (15 ml) and dimethylformamide (5 drops) was added dropwise oxalyl chloride (1.2 ml, 13.76 mmole) under an atmosphere of nitrogen. After the addition was complete, the solution was stirred at room temperature for 2 hours. The solvent was evaporated by a stream of nitrogen. The residue was dried in vacuo at room temperature for one hour to give title acid chloride compound (478 mg, 98.1%) as a gum. This was unstable to moisture and was used immediately without characterization.

H.

2-[4-[4-[(N-Hydroxy-N-Methylamino)carbonyl]-phenyl]butyl]benzoic acid, methyl ester To a stirred solution of N-methyl hydroxylamine hydrochloride (362 mg, 4.33 mmole) and triethylamine (2 ml, 15 mmole) in a mixture of tetrahydrofuran (10 ml) and water (3 ml) was added dropwise a solution of Part G acid chloride compound (478 mg, 1.44 mmole) in 10 ml of dry tetrahydrofuran. After 2.0 hours, the mixture was acidified with 5% hydrochloric acid to pH=2.5, concentrated in vacuo to remove most of the tetrahydrofuran, saturated with sodium chloride and extracted with ethyl ether (3×50 ml). The combined ether extracts were dried over anhydrous MgSO$_4$ and evaporated in vacuo to give 433 mg (87.8%) of title hydroxamic acid compound as an oil with a consistent H$^1$-NMR spectrum. It was homogeneous by tlc.

I.

2-[4-[4-[(N-Hydroxy-N-Methylamino)carbonyl]-phenyl]butyl]benzoic acid

A solution of Part H hydroxamic acid compound (413 mg, 1.21 mmole) in a mixture of methanol (10 ml) and water (1.5 ml) was refluxed with sodium hydroxide (3M, 1.5 ml) under an atmosphere of nitrogen for 2 hours. The resulting solution was cooled to room temperature, acidified with 5% hydrochloric acid, concentrated in vacuo to remove most of the solvents, saturated with sodium chloride and extracted with ethyl ether (4×50 ml). The combined ether extracts were dried over anhydrous MgSO$_4$ and evaporated in vacuo to give a gummy residue. This was chromatographed on a silica gel (30 g, Baker 60–200 mesh) column eluting with dichloromethanemethanol (98:2) to give slightly impure (tlc) title compound. Two recrystallizations of this from ethyl ether gave 255 mg (64.4%) of a tlc-homogeneous analytical specimen, m.p. 94°–95° with consistent mass, IR (1690 cm$^{-1}$, 1612 cm$^{-1}$, C=O strong), H$^1$-NMR and C$^{13}$-NMR spectral data.

Anal. Calc'd for C$_{19}$H$_{21}$NO$_4$: Calc'd: 69.70; H, 6.47; N, 4.28; Found: 69.65; H, 6.51; N, 4.11.

EXAMPLE 2

4-[4-[4-[(N-Hydroxy-N-Methylamino)carbonyl]-phenyl]butyl]benzoic acid

A.

α-Bromo-p-toluic acid, benzyl ester

A mixture of α-bromo-p-toluic acid (10.75 g, 50 mmole; Aldrich Chemical Co.), benzyl alcohol (5.4 g, 50 mmole), dicyclohexylcarbidiimide (10.3 g, 50 mmole) and 4-dimethylaminopyridine (50 mg) in a mixture of dry ether (200 ml) and dry THF (50 ml) was stirred at room temperature for 8.0 hours. The resulting solid was removed by filtration and washed with small amounts of ether. The filtrate and washings were combined, evaporated and the residue was filtered through a column of silica gel (Baker, 60–200 mesh, 100 g) using Et$_2$O-hexane (2:8) for elution to isolate title ester as a homogeneous (tlc) oil (14.0 g, 92%) with a consistent H$^1$-NMR spectrum.

B.

[[[4-(Benzyloxy)carbonyl]phenyl]methyl]triphenyl phosphonium bromide

A stirred solution of Part A ester (4.2 g, 13.8 mmole) and triphenylphosphine (3.6 g, 13.8 mmole) in dry benzene (100 ml) was refluxed for 8.0 hours under an atomsphere of nitrogen resulting in the precipitation of title ester compound. After cooling to room temperature, the mixture was filtered, the solid was washed with small amounts of ether and dried in vacuo to afford title ester compound as a colorless solid (6.9 g, 88.5%).

C.

4-Hydroxypropylbenzoic acid, methyl ester

To a solution of Example 1 Part B acid compound (750 mg, 4.16 mmole) in a mixture of dichloromethane (50 ml) and methanol (10 ml) was added a solution of ethereal diazomethane until the yellow color persisted. After stirring for 30 minutes, the excess diazomethane was destroyed by a few drops of glacial acetic acid. The solvent was evaporated in vacuo to give 800 mg (99.0%, oil) of title ester compound with a consistent H¹-NMR spectrum.

D.

3-[[4-(Methoxycarbonyl)]phenyl]propionaldehyde

To a stirred mixture of pyridinium chlorochromate (6.0 g), dried Celite (6.0 g) and anhydrous sodium acetate (365 mg) in dry chloromethane (30 ml) under dry nitrogen was added a solution of Part C ester compound (1.5 g, 7.72 mmole) in dry dichloromethane (20 ml). After 1.75 hours, the mixture was diluted with ether (100 ml). The supernatant was decanted and the procedure was repeated once again with ether (100 ml). The combined supernatant solutions were washed successively with 0.2M $KH_2PO_4$ (9 ml), $H_2O$ (9.0 ml), 5% $CuSO_4$ (9 ml), $H_2O$ (9.0 ml), 1N $KHCO_3$ (9.0 ml) and $H_2O$ (9.0 ml), dried ($MgSO_4$) and evaporated. The residual oil was filtered through a column of silica gel (25 g, Baker 60–200 mesh) using $Et_2O$-hexane (1:1) for elution to isolate title compound as an oil (1.12 g, 76%) with a consistent H¹-NMR spectrum.

E.

4-[4-[4-[(Benzyloxy)carbonyl]phenyl]-]1-butenyl]benzoic acid, methyl ester

To a cooled (ice-bath) and stirred suspension of the Part B phosphonium salt (4.4 g, 7.76 mmole) in dry THF (35 ml) was added 1.75M n-BuLi in hexane (4.0 ml, 7.0 mmole). The resulting light red suspension was stirred for 2.0 hours and a solution of the Part D aldehyde (1.25 g, 6.5 mmole) in dry THF (4.0 ml) was added. After 30 minutes, the ice bath was removed and the mixture was stirred at room temperature for 4.0 hours. The excess reagent was destroyed by the addition of a few drops of acetic acid. The mixture was then evaporated to leave a solid. This was dissolved in the minimum amount of warm ethyl acetate (discarding the insoluble solids) and applied on a flash-chromatography column (LPS-1 silica gel). Elution of the column with EtOAc-hexane (1:9) afforded title ester compound as a homogeneous (tlc, silica gel, Rf=0.45; EtOAc-hexane, (1:4) colorless solid (2.1 g,; 81%) with a consistent H¹-NMR spectrum).

F.

4-[4-[4-(Carboxy)phenyl]butyl]benzoic acid, methyl ester

A solution of Part E acid compound (1.35 g, 3.37 mmole) in methanol (150 ml, warmed to dissolve and cooled to room temperature) containing 5% Pd/C (30 mg) was stirred under an atmosphere of hydrogen for 1.5 hours. The mixture was then filtered through a bed of Celite, washing the Celite with small amounts of methanol. The filtrate and the washings were combined and evaporated to afford title acid compound as a solid (1.0 g, 95%) with consistent H¹- and C¹³-NMR spectral data. It was homogeneous by tlc (Rf=0.38, silica gel, $CH_3OHCHCl_3$5:95) and can be crystallized from EtOAc or EtOAc-hexane.

G.

4-[4-[4-[(N-Hydroxy-N-Methylamino)carbonyl]-phenyl]butyl]benzoic acid, methyl ester To a cooled (ice-bath) and stirred suspension of the Part F acid (1.0 g, 3.21 mmole) in benzene (10 ml) and chloroform (10 ml) was added oxalylchloride (1.0 ml) followed dropwise by a solution of DMF (0.2 ml) in benzene (1.0 ml). After stirring at room temperature for 1.0 hour, most of the solvents were removed under a jet of nitrogen and the residue was dried in vacuo (50°, 0.5 hour, 0.3 mm). The residual acid chloride was dissolved in dry THF (5.0 ml) and added into a chilled (ice-bath) and stirred solution of $CH_3NHOH.1HCl$ (535 mg, 6.4 mmole) and $Et_3N$ (1.77 ml, 12.8 mmole) in 75% THF (20 ml). The mixture was then warmed to room temperature, evaporated in vacuo, diluted with brine (50 ml) and 10% hydrochloric acid (15 ml) and extracted with ethyl acetate (3×50 ml). The extracts were combined, washed with brine (2×20 ml), dried ($MgSO_4$ anhydrous) and evaporated to afford a solid (1.1 g). One crystallization of this from ethyl acetate-hexane gave a specimen of title hydroxamic acid (900 mg, 83%), m.p. 123°–124°, with consistent H¹- and C¹³-NMR spectral data.

H.

4-[4-[4-[(N-Hydroxy-N-Methylamino)carbonyl]-phenyl]butyl]benzoic acid

A solution of Part G hydroxamic acid compound (850 mg, 2.49 mmole) in methanol (30 ml) containing water (5.0 ml) and 3M NaOH (2.5 ml) was refluxed under an atmosphere of nitrogen for 30 minutes. It was then cooled to room temperature, acidified and concentrated in vacuo. The concentrate was diluted with water, the solids present were isolated by filtration, washed with water (2×10 ml) and dried to afford the title compound as a powder (800 mg, 98.2%). One crystallization of this from ethyl acetate followed by drying (80°, 0.3 mm, 4.0 hours) gave an analytical specimen of title compound as a homogeneous (tlc) colorless solid (670 mg, 81%), m.p. 165°–166° with consistent mass, IR (1674 cm⁻¹, 1610 cm⁻¹, 1600 cm⁻¹, all strong, C=O), H¹-NMR and C¹³-NMR spectral data.

Anal. Calc'd for $C_{19}H_{21}NO_4$: Calc'd: C, 69.70; H, 6.47; N, 4.29; Found: C, 69.61; H, 6.46; N, 4.24.

EXAMPLE 3

N-Hydroxy-N-methyl-4-[4-(4-pyridinyl)butyl]benzamide

A.

4-(3-Bromopropyl)benzoic acid

A gummy complex of triphenyl phosphine (3.16 g, 12 mmole) and N-bromosuccinimide (2.14 g, 12 mmole) was prepared by stirring in benzene (35 ml) in an ice bath for 10 minutes and at room temperature for 1.0 hour. A solution of 4-(3-hydroxypropyl)benzoic acid (1.08 g, 6.0 mmole) in dry $CH_2Cl_2$ (15 ml) was added and the stirring was continued for 30 minutes. The mixture was then concentrated in vacuo, diluted with $Et_2O$ (50 ml) and a solution of sodium carbonate (1.27 g, 12 mmole) in water (50 ml) and stirred vigorously. The $Et_2O$ layer was then separated and the aqueous layer was extracted once again with $Et_2O$ (30 ml). The extracts were discarded. The aqueous layer was acidified with 10% hydrochloric acid and extracted with $Et_2O$ (2×30 ml). The extracts were combined, washed with water (2×10 ml), dried ($MgSO_4$ anhydrous) and evaporated to afford the title compound which was slightly impure (tlc). It was chromatographed on a column of silica gel (Baker 60–200 mesh, 25 g), eluting the column with hexane and $Et_2O$-hexane mixtures (1:4, 1:3, 1:1) to isolate the title compound as a colorless solid (1.2 g, 83%). One crystallization from Et$_2$O-hexane gave 1.0 g, m.p. 116°–117°. The H$^1$-NMR spectrum was consistent with the structure.

B.

4-(3-Bromopropyl)benzoic acid, methyl ester

To a solution of 1.0 g (4.10 mmole) of Part A acid compound in 100 ml of dichloromethane was added an ethereal solution of diazomethane until the yellow color of the solution persisted. The solution was stirred for 30 minutes and the excess diazomethane was destroyed by a few drops of glacial acetic acid. The solvent was evaporated in vacuo to give the tlc-homogeneous title compound (1.05 g, 99.6%, oil) with a consistent H$^1$-NMR spectrum.

C.

[3-[4-(Methoxycarbonyl)phenyl]propyl]triphenyl phosphonium bromide

A mixture of Part B ester compound (1.05 g, 4.08 mmole) and triphenylphosphine (1.07 g, 4.08 mmole) in 20 ml of dry acetonitrile was refluxed under nitrogen for 24 hours. The solvent was evaporated by a stream of nitrogen. The gummy residue was rinsed with ethyl ether (2×50 ml). The ether was decanted and the gummy residue solidified. The white solid was dried at 75° over P$_2$O$_5$ in vacuo overnight to give title compound (1.57 g, 74.1%) with a consistent H$^1$-NMR spectrum.

D.

4-[4-(4-Pyridinyl)-2-butenyl]benzoic acid, methyl ester and

E.

4-[4-(4-Pyridinyl)-2-butenyl]benzoic acid, t-amyl ester

A stirred suspension of Part C compound (1.56 g, 3 mmole) in 20 ml of dry tetrahydrofuran was cooled to 0° (ice-water bath) under nitrogen and then a solution of K-t-amylate (1.7M in toluene) was added dropwise. The suspension became an orange-red solution. This was warmed to room temperature, stirred for 30 minutes and rechilled to 0°. A solution of 4-pyridinecarboxaldehyde (257 mg, 2.4 mmole) in 2 ml of dry tetrahydrofuran was added dropwise. The solution was gradually warmed up to room temperature, stirred for 2 hours and the pH was adjusted to 5.5 with 5% hydrochloric acid. The tetrahydrofuran was mostly removed in vacuo. The residue was diluted with 20 ml of water, saturated with sodium chloride and extracted with ethyl ether (3×50 ml). The combined ether extracts were dried over anhydrous MgSO$_4$ and evaporated in vacuo to give an oil. This was chromatographed on a silica gel (100 g, Baker 60–200 mesh) column, eluting successively with chloroform, ethyl acetate-chloroform (1:1) and ethyl acetate to give 720 mg (oil) of title compounds. On the basis of H$^1$-NMR spectrum, it was a mixture of the methyl and t-amyl esters.

F.

4-[4-(4-Pyridinyl)butyl]benzoic acid, methyl ester and

G.

4-[4-(4-Pyridinyl)butyl]benzoic acid, t-amyl ester

A mixture of Part D and E compounds (720 mg) and 10% palladium on carbon (200 mg) in 40 ml of methanol was hydrogenated at room temperature under atmospheric pressure for 1.5 hours. The resulting solution was filtered through a bed of HYFLO and washed with a small amount of methanol. The filtrate and washing were evaporated in vacuo to give 720 mg of title compound as an oil. On the basis of H$^1$-NMR spectrum (the olefinic protons had disappeared), it was a mixture of the methyl and t-amyl esters.

H.

4-[4-(4-Pyridinyl)butyl]benzoic acid

A mixture of Parts F and G compounds (720 mg) and 3M sodium hydroxide solution (5 ml) in a mixture of methanol (20 ml) and water (1 ml) was refluxed for 5 hours under an atmosphere of nitrogen. The methanol was removed in vacuo. The residue was diluted with water (25 ml) and extracted with ethyl ether to remove non-acidic impurities. The pH of the aqueous solution was adjusted to 5.5 with 5% hydrochloric acid. The precipitated solid was filtered off, washed with a small amount of water and dried at 100° over P$_2$O$_5$ in vacuo overnight to give 406 mg of title acid compound as a solid with a consistent H$^1$-NMR spectrum.

I.

4-[4-(4-Pyridyl)butyl]benzoyl chloride

To a stirred and chilled (0°, water ice bath) suspension of Part H acid compound (300 mg, 1.175 mmole) in a mixture of dry benzene (10 ml) and dimethylformamide (3 drops) was added dropwise oxalyl chloride (1.03 ml, 11.75 mmole) under nitrogen. After the addition was complete, the mixture was stirred at room temperature for 5 hours. The solvent was evaporated by a stream of nitrogen and the residue was dried in vacuo at room temperature for one hour to give 305 mg (89.6%) of title acid chloride compound as a solid. This was unstable to moisture and used immediately without characterization.

J.

N-Hydroxy-N-methyl-4-[4-(4-pyridinyl)butyl]benzamide

To a stirred solution of N-methylhydroxylamine hydrochloride (264 mg, 3.16 mmole) and triethylamine (0.9 ml, 6.46 mmole) in a mixture of tetrahydrofuran (6 ml) and water (2ml) was added dropwise a solution of Part I acid chloride compound (305 mg, 1.053 mmole) under nitrogen. After stirring overnight at room temperature, the pH of the solution was adjusted to 5.5 with 5% hydrochloric acid. The tetrahydrofuran was mostly removed in vacuo. The residue was extracted with dichloromethane (2×50 ml). The combined dichloromethane extracts were dried over anhydrous MgSO$_4$ and evaporated in vacuo to give a solid. This was chromatographed on a silica gel (40 g, Baker 60–200 mesh) column eluting successively with dichloromethane and methanol-dichloromethane (2:98) to give 235 mg of title compound. Crystallization from dichloromethane-hexane gave 185 mg (61.8%) of the tlc-homogeneous analytical specimen, m.p. 148°–150°, with consistent MS, IR (1610 cm$^{-1}$, C=O, strong; 3431 cm$^{-1}$, OH, strong), H$^1$-NMR and C$^{13}$-NMR spectral data.

Anal. Calc'd for C$_{17}$H$_{20}$N$_2$O$_2$ with 0.34 mole water; Calc'd: C, 70.30; H, 7.18; N, 9.64; Found: C, 70.30; H, 7.04; N, 9.49.

EXAMPLE 4

4,4'-(1,4-Butanediyl)bis(N-hydroxy-N-methylbenzamide)

A.

[[[4-(Methoxy)carbonyl]phenyl]methyl]triphenyl phosphonium bromide

A suspension of α-bromo p-toluic acid (5.0 g, 23.3 mmole) in ether (75 ml) was treated with an excess amount of diazomethane in ether and stirred at room temperature for 2 hours. The excess diazomethane was blown off with a stream of nitrogen and the colorless solution concentrated down to an oil which was chromatographed (gravity) on a silica gel column (Baker, 60–200 mesh, 200 ml). The column was eluted with ether-hexane mixtures (1:9, 1:4) and the fractions containing the desired product were combined and evaporated to dryness. The residual ester (5.38 g, 23.3 mmole) and triphenylphosphine (6.17 g, 23.3 mmole) were refluxed in benzene (170 ml) for 8 hours under nitrogen and cooled. The white precipitates obtained were filtered off, washed with a small amount of ether and dried in vacuo (pump) for 5 hours to give title compound as a solid (10.49 g, 91.6%) with a consistent H$^1$-NMR spectrum.

B.

4-[4-[4-(Methoxy)carbonyl]phenyl]-2-butenyl benzoic acid, methyl ester

A cooled (ice-bath) suspension of Part A compound (2.14 g, 4.35 mmole, 1.19 equiv.) and 1.6M n-butyllithium (2.45 ml, 3.92 mmole, 1.08 equiv.) in dry tetrahydrofuran (20 ml) was stirred at 0° under nitrogen for 2 hours. The reddish-orange suspension was then treated with a solution of

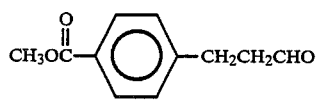

(prepared as described in Example 2 Part D) in dry tetrahydrofuran (3 ml), stirred at 0° for 30 minutes then at room temperature for 2.5 hours. The mixture was treated dropwise with glacial acetic acid until the yellow color disappeared and evaporated to dryness. The residual solid was triturated with warm ethyl acetate (75 ml) and filtered, washing the insoluble precipitates with a small amount of ethyl acetate. The filtrate was evaporated and the semi-solid obtained was chromatographed (flash) on a silica gel column to give the title compound as a liquid (694.3 mg, 58.8%) with consistent H$^1$- and C$^{13}$-NMR spectral data.

C.

4-[4-[4-(Methoxy)carbonyl]phenyl]butyl benzoic acid, methyl ester

A solution of Part B compound (694.3 mg, 2.14 mmole) in dry methanol (100 ml) was treated with 5% Pd/c (20 mg) and hydrogenated at room temperature for 2 hours. The suspension was filtered through a Celite pad and the filtrate evaporated to give title compound as a homogeneous (tlc) oil (690.6 mg, 98.9%) with consistent H$^1$- and C$^{13}$-NMR spectral data.

D.

4,4'-(1,4-Butanediyl)bis-benzoic acid

A solution of Part C compound (690.6 mg, 2.12 mmole) in methanol (25 ml) and water (4 ml) was treated with 50% NaOH (0.5 ml, 6.24 mmole) and refluxed under nitrogen for 1.5 hours. The reaction mixture was cooled, diluted with water (25 ml) and acidified with 2.5N HCl (3.3 ml). The methanol was evaporated off and the aqueous slurry extracted twice with dichloromethane (50 ml). The organic phase was washed with brine (20 ml), dried (anhydrous MgSO$_4$), filtered and evaporated to dryness. The crude product was recrystallized from a combined solution of ethyl acetate and methanol to give title compound as a homogeneous (tlc) solid (516.4 mg, 81.6%, m.p. 275°–280°).

E.

4,4'-(1,4-Butanediyl)bis(N-hydroxy-N-methylbenzamide)

A solution of Part D compound (516 mg, 1.73 mmole) in dry benzene (20 ml) was cooled down to 0° and treated with oxalyl chloride (4 ml) followed by a solution of dimethylformamide (3 drops) in dry benzene (2.0 ml). The mixture was stirred at 0° for ~10 minutes then at room temperature for one hour. The excess oxalyl chloride and benzene were blown off with a stream of nitrogen in a warm bath and the residue was dried in vacuo (pump) for one hour.

The above acid chloride was dissolved in dry tetrahydrofuran (10 ml) and added to a cooled (ice-water bath) solution of methylhydroxylamine hydrochloride (1.18 g) and triethylamine (3.82 ml, 16 equiv.) in tetrahydrofuran (8 ml) and water (8 ml). The mixture was stirred at 0° for 30 minutes, at room temperature for 3.5 hours, diluted with water (60 ml) and adjusted to pH 5.0 with 2.5N HCl (~5.5 ml). The aqueous solution was extracted three times with dichloromethane (150 ml) and the organic extract was washed with brine (50 ml), dried (anhydrous MgSO$_4$), filtered and evaporated to dryness. The crude product showed two carbonyl peaks, one due to carboxylic acid, by infrared spectroscopy, so the entire amount (690 mg) was dissolved in dichloromethane (250 ml) containing some methanol, washed several times with saturated NaHCO$_3$ solution and brine (25 ml). The organic phase was dried (anhydrous MgSO$_4$) and evaporated to give title compound as a colorless solid (350 mg, 56.8%, m.p. 157°–159°) after drying in vacuo (0.5 mm) at 60° for 18 hours, with consistent analytical, MS, IR (1597 cm$^{-1}$, strong, C=O, 3162 cm$^{-1}$, strong, OH), H$^1$- and C$^{13}$-NMR spectrum.

EXAMPLE 5

3-[4-[4-[(Hydroxymethylamino)carbonyl]phenyl]butyl]benzoic acid

By following the procedure of Example 1, but replacing o-toluic acid with m-toluic acid in Part A(1), the title compound can be prepared.

EXAMPLE 6

N-Acetyloxy-N-methyl-4-[4-(4-pyridinyl)butyl]benzamide

A solution of 200 mg of N-hydroxy-N-methyl-4-[4-(4-pyridinyl)butyl]benzamide in dry pyridine (3.0 ml) was mixed with acetic anhydride (0.5 ml) and was allowed to stand at room temperature for 20 hours. The mixture was then concentrated in vacuo, diluted with dichloromethane, washed with a dilute $Na_2CO_3$ solution and water, dried ($MgSO_4$ anhydrous), evaporated and the residue was purified by column chromatography on silica gel to afford the title compound.

EXAMPLE 7

N-Benzoyloxy-N-methyl-4-[4-(4-pyridinyl)butyl]benzamide

By following the procedure of Example 6 but replacing acetic anhydride with benzoyl chloride and carrying out the reaction at a lower temperature (0°), the title compound can be prepared.

EXAMPLES 8 to 26

Following the procedures outlined in the specification and the working Examples, the following exemplary compounds in accordance with the present invention may be prepared.

| Ex. No. | Z (position) | m | R¹ | R² |
|---|---|---|---|---|
| 8. | 4-pyridinyl | 3 | H | $CH_3$ |
| 9. | 3-pyridinyl | 4 | $C_2H_5$ | $-C(=O)-C_6H_5$ |
| 10. | 2-pyridinyl | 5 | $C_6H_5$ | $C_2H_5$ |
| 11. | 4-pyridinyl (different position) | 6 | $-CH=CHCH_3$ | H |
| 12 | 3-methyl-4-$HO_2C$-phenyl | 3 | cyclohexyl | $CH_3$ |
| 13 | 3-methyl-4-$HO_3C$-phenyl | 5 | $-CH_2-C_6H_5$ | cyclohexyl |
| 14. | 4-$HO_2C$-phenyl | 7 | H | H |
| 15. | 3-methyl-4-$HO_2C$-phenyl | 8 | $C_3H_7$ | $-C(=O)C_2H_5$ |

-continued
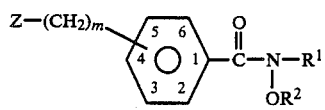
| Ex. No. | Z (position) | m | R¹ | R² |
|---|---|---|---|---|
| 16. | 2-HO₂C-C₆H₄- | 4 | $C_6H_5$ | $CH_3$ |
| 17. | 2-pyridyl | 6 | $-CH_2-CH=CHCH_3$ | $C_2H_5$ |
| 18. | 3-methyl-pyridyl | 8 | cyclohexyl | $C_4H_9$ |
| 19. | 4-pyridyl | 2 | $-CH_2-C_6H_5$ | $\underset{\text{O}}{\overset{\|}{C}}-C_3H_7$ |
| 20. | 4-pyridyl | 3 | $-(CH_2)_2$ | H |
| 21. | 4-(HO-NH-C(O)-)-C₆H₄- | 6 | $-CH=CHCH_3$ | H |
| 22. | 3-(CH₃-N(OC₂H₅)-C(O)-)-C₆H₄- | 3 | cyclopentyl | $CH_3$ |
| 23. | 2-(C₃H₇-N(O-cyclohexyl)-C(O)-)-C₆H₄- | 5 | $-CH_2-C_6H_5$ | cyclohexyl |
| 24. | 4-(C₄H₉-N(O-C(O)C₂H₅)-C(O)-)-C₆H₄- | 7 | H | $\underset{\text{O}}{\overset{\|}{C}}C_2H_5$ |

-continued

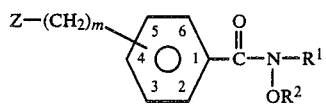

| Ex. No. | Z (position) | m | R¹ | R² |
|---|---|---|---|---|
| 25. | 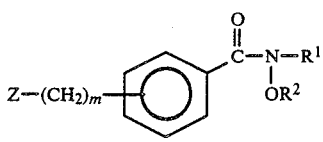 | 8 | $C_3H_7$ | $\underset{\underset{CC_6H_5}{\|}}{O}$ |
| 26. | 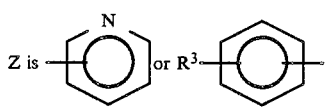 | 4 | $C_6H_5$ | $CH_3$ |

What is claimed is:

1. A compound having the structure

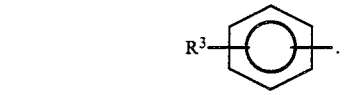

wherein
$R^1$ is H, alkyl, aryl, lower alkenyl having 3 to 8 carbons, cycloalkyl having 3 to 12 carbons, or arylalkyl;
$R^2$ is H, alkyl, aryl, cycloalkyl having 3 to 12 carbons, alkanoyl or aroyl;
m is 2 to 8;

Z is 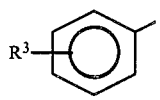

wherein
$R^3$ is COOH; and
$(CH_2)_m$ is unsubstituted or substituted with 1 or 2 alkyl and/or 1 or 2 halogen substituents;
and where Z is

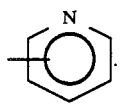

including pharmaceutically acceptable basic salts thereof, wherein the term alkyl by itself or as part of another group is a straight chain or branched chain radical having 1 to 12 carbons and is unsubstituted or substituted with halogen, $CF_3$, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio; and the term aryl by itself or as part of another group is a monocyclic or bicyclic aromatic group having 6 to 10 carbons in the ring portion and is unsubstituted or substituted with 1 or 2 alkyl groups, 1 or 2 halogens, 1 or 2 alkoxy groups, an aryl group, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

2. The compound as defined in claim 1 wherein $R^1$ is alkyl.

3. The compound as defined in claim 1 wherein $R^1$ is alkyl and $R^2$ is H.

4. The compound as defined in claim 1 wherein Z is

5. The compound as defined in claim 4 wherein $R^3$ is o- or p-$CO_2H$.

6. The compound as defined in claim 1 wherein Z is

7. The compound as defined in claim 1 having the name N-hydroxy-N-methyl-4-[4-(4-pyridinyl)butyl]-benzamide.

8. The compound as defined in claim 1 having the name 2-[4-[4-[(N-hydroxy-N-methylamino)carbonyl]-phenyl]butyl]benzoic acid.

9. The compound as defined in claim 1 having the name 4-[4-[4-[(N-hydroxy-N-methylamino)carbonyl]-phenyl]butyl]benzoic acid.

10. A composition for inhibiting allergic conditions in a mammalian species, comprising an effective amount of a compound as defined in claim 1 or a pharmaceutically acceptable salt thereof, and a pharmaceutically acceptable carrier therefor.

11. A method of treating allergy of a reagin or non-reagin nature, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A method for treating asthma in a mammalian species in need of such treatment, which comprises administering to a mammalian host an effective amount of a compound as defined in claim 1 or a pharmaceutically acceptable salt thereof.

* * * * *